US007177671B2

(12) United States Patent
Nabetani

(10) Patent No.: US 7,177,671 B2
(45) Date of Patent: *Feb. 13, 2007

(54) RF COIL, RF SIGNAL TRANSMITTER RECEIVER, RF SIGNAL RECEIVER, AND MAGNETIC RESONANCE IMAGING SYSTEM FOR THE INFERIOR ABDOMEN

(75) Inventor: Akira Nabetani, Tokyo (JP)

(73) Assignee: GE Medical Systems Global Technology Company, LLC, Waukesha (DE)

( * ) Notice: Subject to any disclaimer, the term of this patent is extended or adjusted under 35 U.S.C. 154(b) by 863 days.

This patent is subject to a terminal disclaimer.

(21) Appl. No.: 10/139,977

(22) Filed: May 7, 2002

(65) Prior Publication Data

US 2002/0169375 A1 Nov. 14, 2002

(30) Foreign Application Priority Data

May 8, 2001 (JP) .............................. 2001-136986

(51) Int. Cl.
*A61B 5/05* (2006.01)
(52) U.S. Cl. ...................................... 600/422; 600/410
(58) Field of Classification Search ................ 600/407, 600/410, 420–422
See application file for complete search history.

(56) References Cited

U.S. PATENT DOCUMENTS

| 4,769,605 | A |   | 9/1988  | Fox |
|-----------|---|---|---------|-----|
| 4,831,330 | A | * | 5/1989  | Takahashi .................... 324/318 |
| 5,144,241 | A |   | 9/1992  | Oppelt et al. |
| 5,144,243 | A |   | 9/1992  | Nakabayashi et al. |
| 5,302,901 | A |   | 4/1994  | Snelten |
| 5,473,251 | A | * | 12/1995 | Mori ........................... 324/318 |
| 5,708,361 | A |   | 1/1998  | Wang et al. |
| 5,842,989 | A | * | 12/1998 | Zur ............................. 600/410 |
| 5,973,495 | A |   | 10/1999 | Mansfield |
| 6,097,186 | A |   | 8/2000  | Nabetani |
| 6,348,794 | B1 |  | 2/2002  | Nabetani et al. |
| 6,591,128 | B1 | * | 7/2003  | Wu et al. .................... 600/422 |
| 6,836,117 | B2 | * | 12/2004 | Tamura et al. .............. 324/318 |
| 6,850,065 | B1 | * | 2/2005  | Fujita et al. ................ 324/318 |
| 6,898,454 | B2 | * | 5/2005  | Atalar et al. ................ 600/410 |
| 2002/0151788 | A1 | * | 10/2002 | Menon ........................ 600/421 |
| 2002/0169375 | A1 | * | 11/2002 | Nabetani ..................... 600/422 |

FOREIGN PATENT DOCUMENTS

| JP | 61-124614 | 12/1986 |
|----|-----------|---------|
| JP | 07-327957 | 12/1995 |
| JP | 2000-185025 | 7/2000 |

* cited by examiner

*Primary Examiner*—Brian L. Casler
*Assistant Examiner*—Sanjay Cattungal
(74) *Attorney, Agent, or Firm*—Carl B. Horton, Esq.; Armstrong Teasdale, .LLP

(57) ABSTRACT

For the purpose of providing an RF coil that enables satisfactory imaging of the prostate, the RF coil is composed of a first saddle coil and a second saddle coil. The first saddle coil has two loop portions opposed to each other so that they can sandwich the inferior abdomen of a human body anteroposteriorly. The second saddle coil has two loop portions opposed to each other so that they will permit insertion of the inferior limbs of a human body thereinto and can sandwich the inferior abdomen thereof laterally.

20 Claims, 10 Drawing Sheets

RF COIL, RF SIGNAL TRANSMITTER RECEIVER, RF SIGNAL RECEIVER, AND MAGNETIC RESONANCE IMAGING SYSTEM FOR THE INFERIOR ABDOMEN

CROSS REFERENCE TO RELATED APPLICATIONS

This application claims the benefit of Japanese Application No. 2001-136986 filed May 8, 2001.

BACKGROUND OF THE INVENTION

The present invention relates to a radio-frequency (RF) coil, an RF signal transmitter-receiver, an RF signal receiver, and a magnetic resonance imaging system. More specifically, the present invention relates to an RF coil, an RF signal transmitter-receiver, an RF signal receiver, and a magnetic resonance imaging system which are used to image the inferior abdomen of a human body through magnetic resonance.

In a magnetic resonance imaging (MRI) system, an object of imaging is transported into a bore of a magnet system, that is, an imaging space in which a static magnetic field is created. Magnetic field gradients and radio-frequency magnetic fields are applied to the object of imaging, whereby spins in the object of imaging induce magnetic resonance (MR) signals. An image is reconstructed based on the received signals.

The radio-frequency magnetic field is applied in the form of RF pulses. The application of RF pulses may be referred to as transmission of an RF signal. The magnetic resonance (MR) signal is received in the form of an RF signal. An RF coil is used to transmit or receive RF signals.

The RF coil may be dedicated to transmission or reception or used in common for transmission and reception. The RF coils dedicated to reception and transmission respectively will therefore have various shapes conformable to regions to be imaged. One of the RF coils is an RF coil used to image the prostate. This RF coil is designed to be a saddle coil that sandwiches the inferior abdomen of an object antero-posteriorly.

The prostate is located at the lowermost position in the inferior abdomen. Despite the use of the foregoing RF coil, an image satisfactorily reflecting a high signal-to-noise ratio cannot be produced all the time.

SUMMARY OF THE INVENTION

Therefore, an object of the present invention is to provide an RF coil, an RF signal transmitter-receiver, an RF signal receiver, and a magnetic resonance imaging system which can image the prostate satisfactorily.

(1) In one aspect of the present invention, there is provided an RF coil including a first saddle coil and a second saddle coil. The first saddle coil has two loop portions opposed to each other so that they can sandwich the inferior abdomen of a human body antero-posteriorly. The second saddle coil has two loop portions opposed to each other so that they will permit insertion of the inferior limbs of a human body thereinto and can sandwich the inferior abdomen thereof laterally.

(2) In another aspect of the present invention, there is provided an RF signal transmitter-receiver including a first saddle coil, a second saddle coil, a driving means, and a synthesizing means. The first saddle coil has two loop portions opposed to each other so that they can sandwich the inferior abdomen of a human body antero-posteriorly. The second saddle coil has two loop portions opposed to each other so that they will permit insertion of the inferior limbs of a human body thereinto and can sandwich the inferior abdomen thereof laterally. The driving means drives the first saddle coil and second saddle coil using a quadrature technique. The synthesizing means synthesizes two radio-frequency (RF) signals received by the first and second saddle coils respectively using the quadrature technique.

(3) In still another aspect of the present invention, there is provided an RF signal receiver including a first saddle coil, a second saddle coil, and a synthesizing means. The first saddle coil has two loop portions opposed to each other so that they can sandwich the inferior abdomen of a human body antero-posteriorly. The second saddle coil has two loop portions opposed to each other so that they will permit insertion of the inferior limbs of a human body thereinto and can sandwich the inferior abdomen thereof laterally. The synthesizing means synthesizes two RF signals received by the first and second saddle coils respectively using a quadrature technique.

(4) In still another aspect of the present invention, there is provided an RF signal receiver including a first saddle coil, a second saddle coil, and a synthesizing means. The first saddle coil has two loop portions opposed to each other so that they can sandwich the inferior abdomen of a human body antero-posteriorly. The second saddle coil has two loop portions opposed to each other so that they will permit insertion of the inferior limbs of a human body thereinto and can sandwich the inferior abdomen thereof laterally. The synthesizing means synthesizes two RF signals received by the first coil and second saddle coil respectively using a phased array technique.

(5) In still another aspect of the present invention, there is provided a magnetic resonance imaging system including a static magnetic field creating means, a magnetic field gradient creating means, an RF signal transmitting/receiving means, and an image producing means. The static magnetic field creating means creates a static magnetic field in a space in which an object of imaging is placed. The magnetic field gradient creating means creates magnetic field gradients in the space. The RF signal transmitting/receiving means transmits RF signals to the space and receives RF signals from the space. The image producing means produces an image according to the received RF signals. In the magnetic resonance imaging system, the RF signal transmitting/receiving means includes a first saddle coil, a second saddle coil, a driving means, and a synthesizing means. The first saddle coil has two loop portions opposed to each other so that they can sandwich the inferior abdomen of a human body antero-posteriorly. The second saddle coil has two loop portions opposed to each other so that they will permit insertion of the inferior limbs of a human body thereinto and can sandwich the inferior abdomen thereof laterally. The driving means drives the first saddle coil and second saddle coil using a quadrature technique. The synthesizing means synthesizes two RF signals received by the first saddle coil and second saddle coil respectively using the quadrature technique.

(6) In still another aspect of the present invention, there is provided a magnetic resonance imaging system including a static magnetic field creating means, a magnetic field gradient creating means, an RF signal transmitting means, an RF signal receiving means, and an image producing means. The static magnetic field creating means creates a static magnetic field in a space in which an object of imaging is placed. The magnetic field gradient creating means creates magnetic field gradients in the space. The RF signal transmitting means transmits RF signals to the space. The RF signal receiving means receives RF signals from the space. The image producing means produces an image according to the received RF signals. In the magnetic resonance imaging system, the RF signal receiving means includes a first saddle coil, a second saddle coil, and a synthesizing coil. The first saddle coil has two loop portions opposed to each other so that they can sandwich the inferior abdomen of a human body antero-posteriorly. The second saddle coil has two loop portions opposed to each other so that they will permit insertion of the inferior limbs of a human body thereinto and can sandwich the inferior abdomen thereof laterally. The synthesizing means synthesizes two RF signals received by the first and second saddle coils respectively using a quadrature technique.

(7) In still another aspect of the present invention, there is provided a magnetic resonance imaging system including a static magnetic field creating means, a magnetic field gradient creating means, an RF signal transmitting means, an RF signal receiving means, and an image producing means. The static magnetic field creating means creates a static magnetic field in a space in an object of imaging is placed. The magnetic field gradient creating means creates magnetic field gradients in the space. The RF signal transmitting means transmits RF signals to the space. The RF signal receiving means receives RF signals from the space. The image producing means produces an image according to the received RF signals. In the magnetic resonance imaging system, the RF signal receiving means includes a first saddle coil, a second saddle coil, and a synthesizing means. The first saddle coil has two loop portions opposed to each other so that they can sandwich the inferior abdomen of a human body antero-posteriorly. The second saddle coil has two loop portions opposed to each other so that they will permit insertion of the inferior limbs of a human body thereinto and can sandwich the inferior abdomen thereof laterally. The synthesizing means synthesizes two RF signals received by the first saddle coil and second saddle coil respectively using a phased array technique.

In the aspects of the present invention set forth in items (1) to (7), an RF coil has the first saddle coil and second saddle coil. The first saddle coil has two loop portions opposed to each other so that they can sandwich the inferior abdomen of a human being antero-posteriorly. The second saddle coil has two loop portions opposed to each other so that they will permit insertion of the inferior limbs of a human body thereinto and can sandwich the inferior abdomen thereof laterally. Consequently, magnetic resonance (MR) signals induced at the prostate can be received by making the most of a high signal-to-noise ratio.

From a viewpoint of improved ease of having an RF coil worn on a human body, the RF coil preferably includes a flexible circuit board that is shaped to be readily worn on a human body and that has a circuit pattern relevant to the first, saddle coil and a circuit pattern relevant to the second saddle coil printed thereon.

(8) In still another aspect of the present invention, there is provided an RF coil having a first coil pair and a second coil pair. The first coil pair includes two loops opposed to each other so that they can sandwich the inferior abdomen of a human body antero-posteriorly. The second coil pair includes two loops opposed to each other so that they will permit insertion of the inferior limbs of a human body thereinto and can sandwich the inferior abdomen thereof laterally.

(9) In still another aspect of the present invention, there is provided an RF signal receiver including a first coil pair, a second coil pair, and a synthesizing means. The first coil pair includes two loops opposed to each other so that they can sandwich the inferior abdomen of a human body antero-posteriorly. The second pair includes two loops opposed to each other so that they will permit insertion of the inferior limbs of a human body thereinto and can sandwich the inferior abdomen thereof laterally. The synthesizing means synthesizes two RF signals received by the first coil pair and second coil pair respectively using a phased array technique.

(10) In still another aspect of the present invention, there is provided a magnetic resonance imaging system including a static magnetic field creating means, a magnetic field gradient creating means, an RF signal transmitting means, an RF signal receiving means, and an image producing means. The static magnetic field creating means creates a static magnetic field in a space in which an object of imaging is placed. The magnetic field gradient creating means creates magnetic field gradients in the space. The RF signal transmitting means transmits RF signals to the space. The RF signal receiving means receives RF signals from the space. The image producing means produces an image according to the received RF signals. In the magnetic resonance imaging system, the RF signal receiving means includes a first coil pair, a second coil pair, and a synthesizing means. The first coil pair has two loops opposed to each other so that they can sandwich the inferior abdomen of a human body antero-posteriorly. The second coil pair has two loops opposed to each other so that they will permit insertion of the inferior limbs of a human body thereinto and can sandwich the inferior abdomen thereof laterally. The synthesizing means synthesizes two RF signals received by the first coil pair and second coil pair respectively using a phased array technique.

In the aspects of the present invention set forth in items (8) to (10), an RF coil is including a first coil pair and a second coil pair. The first coil pair has two loops opposed to each other so that they can sandwich the inferior abdomen of a human body antero-posteriorly. The second coil pair has two loops opposed to each other so that they will permit insertion of the inferior limbs of a human body thereinto and can sandwich the inferior abdomen thereof laterally. Consequently, magnetic resonance (MR) signals induced at the prostate can be received by making the most of a high signal-to-noise ratio.

From a viewpoint of improved ease of having an RF coil worn on a human body, the RF coil preferably includes a flexible circuit board that is shaped to be readily worn on the inferior abdomen of a human body and that has a circuit pattern relevant to the first coil pair and a circuit pattern relevant to the second coil pair printed thereon.

According to the present invention, there are provided an RF coil, an RF signal transmitter-receiver, an RF signal receiver, and a magnetic resonance imaging system that enable satisfactory imaging of the prostate.

Further objects and advantages of the present invention will be apparent from the following description of the preferred embodiments of the invention as illustrated in the accompanying drawings.

DETAILED DESCRIPTION OF THE INVENTION

Figure 1:
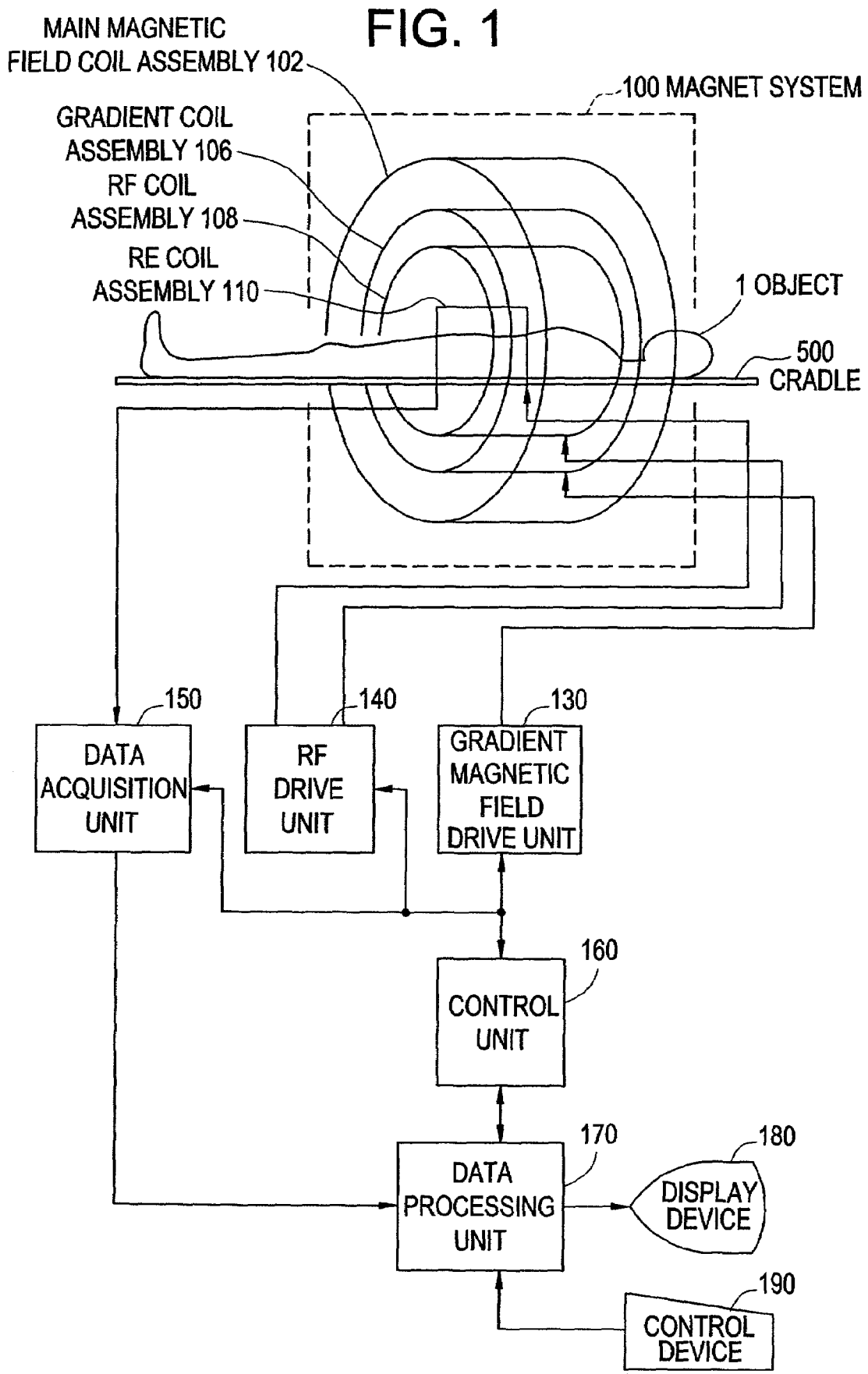
FIG. 1 is a block diagram of a system that is an example of an embodiment of the present invention.

An embodiment of the present invention will be described with reference to drawings below. FIG. 1 is a block diagram showing a magnetic resonance imaging system. The system is the embodiment of the present invention. The system configuration provides an example of the embodiment of the system in accordance with the present invention.

As illustrated, the system includes a magnet system 100. The magnet system 100 includes a main magnetic field coil assembly 102, a gradient coil assembly 106, and a radio-frequency (RF) coil assembly 108. These coil assemblies have almost the same cylindrical shape and are arranged coaxially.

An object of imaging 1 lying down on a cradle 500 is transported to or from the substantially cylindrical bore of the magnet system 100 by a transporting means that is not shown. The object 1 wears an RF coil assembly 110 on the inferior abdomen thereof. The RF coil assembly 110 will be described later.

The main magnetic field coil assembly 102 creates a static magnetic field in the bore of the magnet system 100. The direction in which the static magnetic field is induced is generally parallel to the direction of the body axis of the subject 1. In other words, a so-called horizontal magnetic field is created. The main magnetic field coil assembly 102 is realized using, for example, a superconductor coil. Needless to say, the present invention is not limited to the superconductor coil. Alternatively, a normal conductor coil or the like will do. The main magnetic field coil assembly 102 is an example of a static magnetic field creating means employed according to the present invention.

The gradient coil assembly 106 creates three magnetic field gradients that are used to bring about a gradient in the strength of a static magnetic field in the directions of three axes perpendicular to one another, that is, an axis for slicing, an axis for phase encoding, and an axis for frequency encoding.

Assuming that the coordinate axes perpendicular to one another in the space of a static magnetic field are x, y, and z axes, any of the axes may be regarded as the axis for slicing. In this case, one of the remaining axes is regarded as the axis for phase encoding, and the other remaining axis is regarded as the axis for frequency encoding. Moreover, the axes for slicing, phase encoding, and frequency encoding may have any slope with respect to the x, y, and z axes while remaining perpendicular to one another. In the present system, the body-axis direction of the object 1 shall be the z-axis direction.

A magnetic field gradient induced in the axial direction for slicing may be referred to as a slicing magnetic field gradient. A magnetic field gradient induced in the axial direction for phase encoding may be referred to as a phase-encoding magnetic field gradient. A magnetic field gradient induced in the axial direction for frequency encoding may be referred to as a readout magnetic field gradient. In order to enable generation of the magnetic field gradients, the gradient coil assembly 106 includes three gradient coils that are not shown.

The RF coil assembly 108 creates a radio-frequency magnetic field, which is used to excite spins in the body of the object 1, in the space of a static magnetic field. Hereinafter, the creation of a radio-frequency magnetic field may be referred to as transmission of an RF excitation signal. Moreover, the RF excitation signal may be termed RF pulses. The RF coil assembly 110 receives electromagnetic waves induced by the excited spins, that is, magnetic resonance (MR) signals. The RF coil assembly 110 may transmit the RF excitation signal.

A gradient drive unit 130 is connected to the gradient coil assembly 106. The gradient drive unit 130 applies a driving signal to the gradient coil assembly 106 and thus causes the gradient coil assembly 106 to generate magnetic field gradients. The gradient drive unit 130 includes three drive circuits, which are not shown, in one-to-one correspondence with the three gradient coils included in the gradient coil assembly 106. The gradient coil assembly 106 and gradient drive unit 130 constitute an example of a magnetic field gradient creating means employed according to the present invention.

An RF drive unit 140 is connected to the RF coil assemblies 108 and 110. The RF drive unit 140 applies a driving signal to the RF coil assembly 108 or RF coil assembly 110, whereby RF pulses are transmitted in order to excite spins in the body of the object 1. The RF coil assemblies 108 and 110 constitute an example of an RF signal transmitting means employed according to the present invention.

A data acquisition unit 150 is connected to the RF coil assembly 110. The data acquisition unit 150 samples signals received by the RF coil assembly 110 and acquires them in the form of digital data. The RF coil assembly 110, RF drive unit 140, and data acquisition unit 150 constitute an example of an RF signal transmitting/receiving means employed according to the present invention.

A control unit 160 is connected to the gradient drive unit 130, RF drive unit 140, and data acquisition unit 150. The control unit 160 controls the gradient drive unit 130, RF drive unit 140, and data acquisition unit 150 so as to accomplish imaging.

The control unit 160 is realized using, for example, a computer or the like. The control unit 160 includes a memory that is not shown. A program for giving instructions to the control unit 160 and various data items are stored in the memory. The ability of the control unit 160 is implemented by running the program stored in the memory under within the computer.

An output terminal of the data acquisition unit 150 is connected to a data processing unit 170. Data acquired by the data acquisition unit 150 is transmitted to the data processing unit 170. The data processing unit 170 is realized using, for example, a computer. The data processing unit 170 includes a memory that is not shown. A program for giving instructions to the data processing unit 170 and various data items are stored in the memory.

The data processing unit 170 is connected to the control unit 160. The data processing unit 170 is an upper-level unit of the control unit 160 and controls the control unit 160. A feature of the present system is implemented by running a program stored in the memory within the data processing unit 170.

The data processing unit 170 stores data acquired by the data acquisition unit 150 in the memory thereof. A data space is defined in the memory. The data space is used as a two-dimensional Fourier space that may be termed a k space. The data processing unit 170 performs two-dimensional Fourier transform on the data in the k space so as to reconstruct an image of the object 1. The data processing unit 170 forms an example of an image producing means employed according to the present invention.

A display device 180 and a control device 190 are connected to the data processing unit 170. The display device 180 is realized with a graphic display or the like. The control device 190 is realized with a keyboard having a pointing device.

The display device 180 displays a reconstructed image provided by the data processing unit 170 and various kinds of information. The control device 190 is manipulated by a user in order to input various commands or information to the data processing unit 170. The user operates the system interactively using the display device 180 and control device 190.

Figure 2:
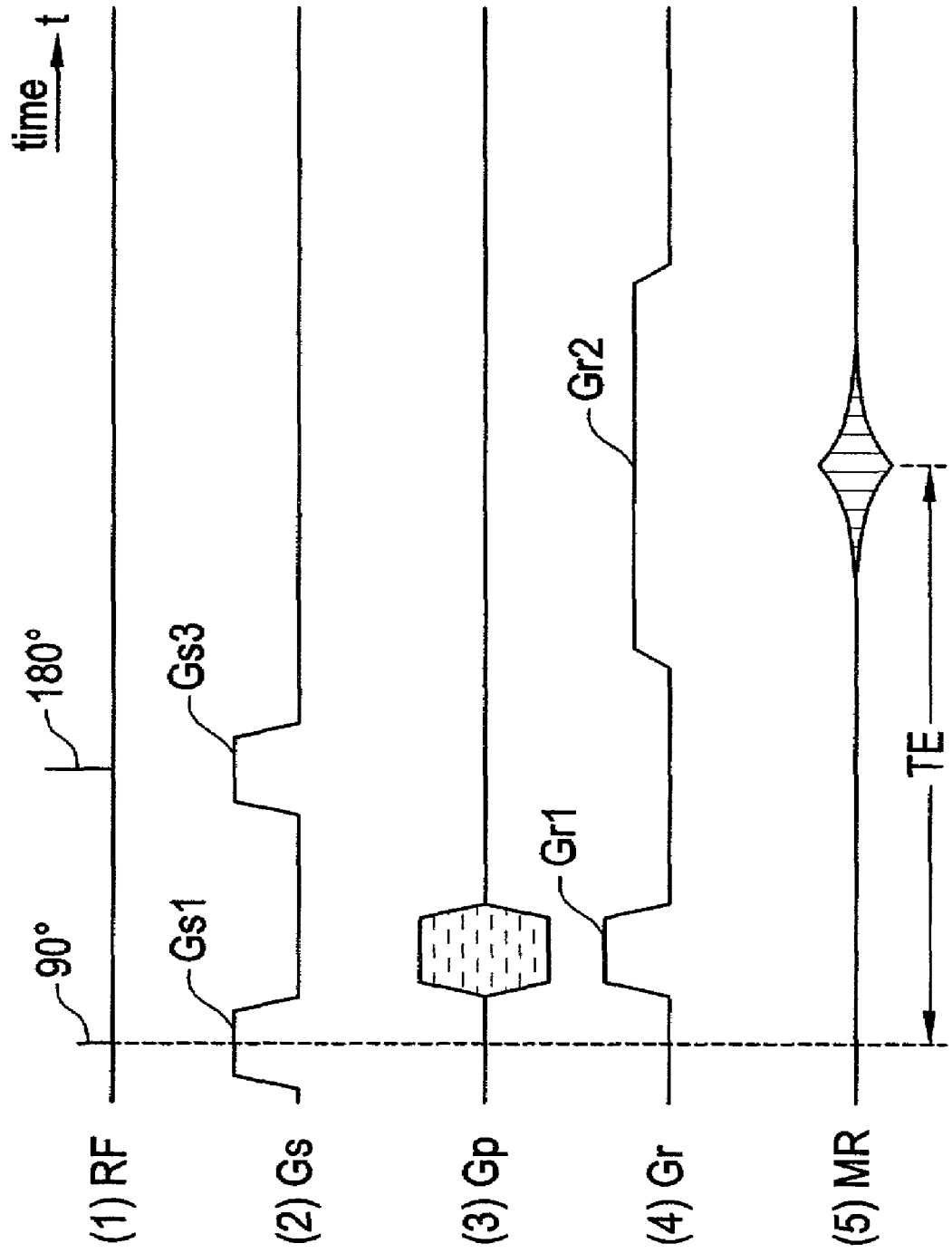
FIG. 2 shows an example of a pulse sequence according to which pulses are applied for magnetic resonance imaging.

Imaging actions to be performed in the present system will be described below. FIG. 2 shows an example of a pulse sequence according to which the present system applies pulses so as to acquire magnetic resonance. The pulse sequence is a pulse sequence adopted for acquiring spin echoes, that is, a pulse sequence employed in spin echo imaging.

Referring to FIG. 2, (1) shows RF pulses, that is, 90° and 180° pulses. (2), (3), (4) and (5) show a slicing magnetic field gradient Gs, a phase-encoding magnetic field gradient Gp, a readout magnetic field gradient Gr, and a spin echo MR. The 90° and 180° pulses are represented by their center values. The pulse sequence progresses along a time axis t from left to right in FIG. 2.

As shown in FIG. 2, the 90° and 180° pulses excite spins by 90° and 180° respectively. During 90° and 180° excitations, slicing magnetic field gradients Gs1 and Gs3 are applied in order to perform selective excitation to select and excite a predetermined plane.

During an interval between the 90° and 180° excitations, a phase-encoding magnetic field gradient Gp is applied in order to perform phase encoding in the axial direction for phase encoding. Moreover, a readout magnetic field gradient Gr1 is applied in order to perform dephasing in the axial direction for frequency encoding.

After completion of the 180° excitation, a readout magnetic field gradient Gr2 is applied in order to perform rephasing. This results in spin echoes MR. The spin echoes MR are detected as RF signals each having a symmetrical wave that is symmetrical with respect to the center of an echo. The center of an echo appears in an echo time TE after 90° excitation. The spin echoes MR are acquired in the form of view data by the data acquisition unit 150.

The pulse sequence is repeated at intervals of a repetition time TR, for example, 64 to 256 times. At every repetition, the phase-encoding magnetic field gradient has the strength thereof changed. Dashed lines conceptually indicate sequential changes in the strength of the phase-encoding magnetic field gradient Gp. This results in view data items that represent 64 to 256 views and are acquired based on the different results of phase encoding performed in the axial direction for phase encoding. The view data is stored in the k space in the memory included in the data processing unit 170.

The data in the k space is subjected to two-dimensional Fourier transform, whereby two-dimensional image data in a real space, that is, a reconstructed image is produced. The image is displayed on the display device 180.

Figure 3:
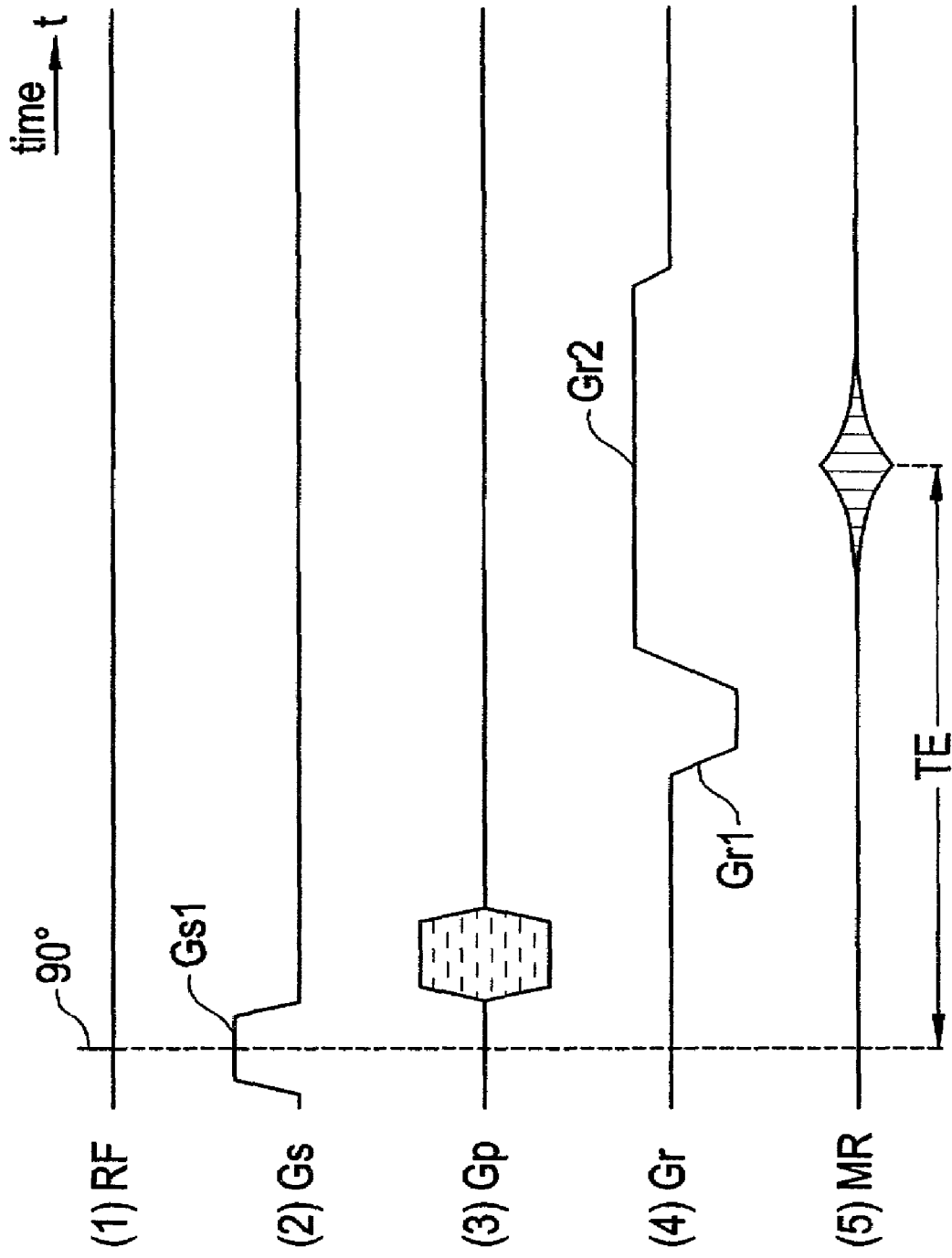
FIG. 3 shows an example of the pulse sequence according to which pulses are applied for magnetic resonance imaging.

FIG. 3 shows another example of a pulse sequence according to which the present system applies pulses so as to acquire magnetic resonance signals. The pulse sequence is employed in acquisition of gradient echoes, that is, in gradient echo imaging.

Referring to FIG. 3, (1) shows an RF pulse, that is, a 90° pulse. (2), (3), (4), and (5) show a slicing magnetic field gradient Gs, a phase-encoding magnetic field gradient Gp, a readout magnetic field gradient Gr, and a gradient echo MR respectively. Incidentally, the 90° pulse is represented by its center value. This pulse sequence progresses along a time axis t from left to right in the drawing.

As seen from FIG. 3, the 90° pulse is used to excite spins by 90°. During the 90° excitation, a slicing magnetic field gradient Gs1 is applied in order to perform selective excitation to select and excite a predetermined plane. After completion of the 90° excitation, the phase-encoding magnetic field gradient Gp is applied in order to perform phase encoding in the axial direction for phase encoding.

Thereafter, a readout magnetic field gradient Gr1 is applied in order to perform dephasing in the axial direction for frequency encoding. A readout magnetic field gradient Gr2 is then applied in order to perform rephasing. This brings about gradient echoes MR.

The gradient echoes MR are detected as RF signals each having a symmetrical waveform that is symmetrical with respect to the center of an echo. The center of an echo appears in the TE after the 90° excitation. The gradient echoes MR are acquired in the form of view data by the data acquisition unit 150.

The pulse sequence is repeated at intervals of the TR, for example, 64 to 256 times. At every repetition, the phase-encoding magnetic field gradient Gp has the strength thereof changed. Dashed lines conceptually indicate the sequential changes in the strength of the phase-encoding magnetic field gradient Gp. This results in view data items that represent 64 to 256 views and are acquired based on the different results of phase encoding performed in the axial direction for phase encoding. The thus acquired view data is stored in the k space in the memory included in the data processing unit 170.

The data in the k space is subjected to two-dimensional Fourier transform, whereby two-dimensional image data in a real space, that is, a reconstructed image is produced. The image is displayed on the display device 180.

Figure 4:
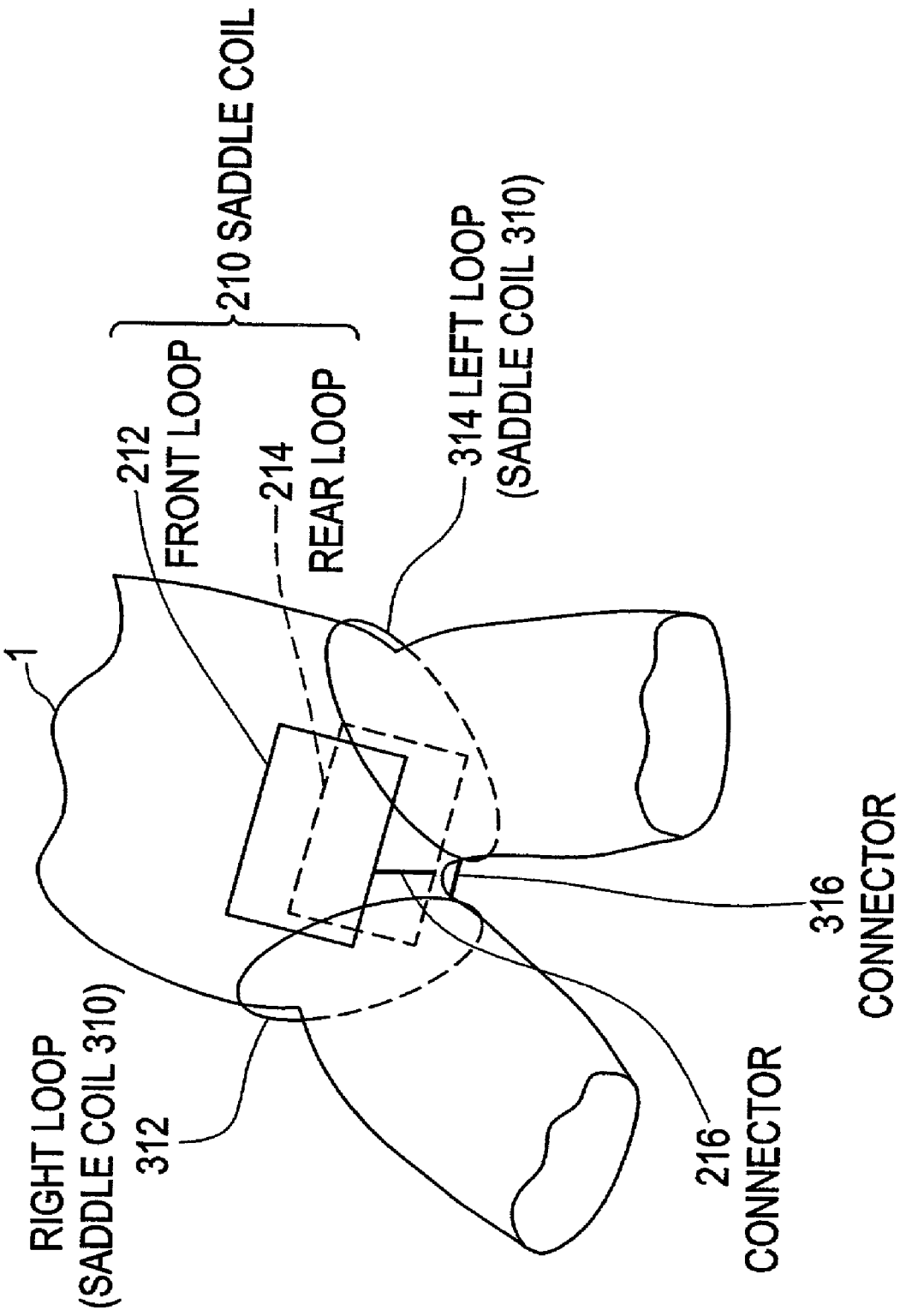
FIG. 4 schematically shows an RF coil worn on an object.
Figure 5:
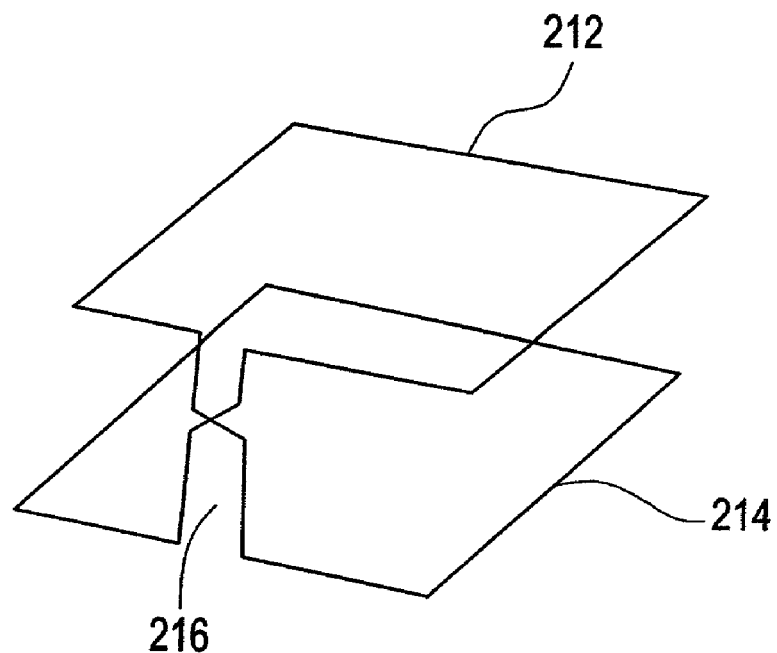
FIG. 5 schematically shows one saddle coil.

FIG. 4 illustratively shows the RF coil assembly 110 worn on the object 1. As illustrated, the RF coil assembly 110 includes a front loop 212 and a rear loop 214 that are opposed to each other with the inferior abdomen of the object 1 sandwiched antero-posteriorly between them. The front loop 212 and rear loop 214 are linked by a connector 216. The connector 216 is, as shown in FIG. 5, composed of two crossing electrical paths, whereby the front loop 212 and rear loop 214 constitute a saddle coil 210 that is a closed loop. The saddle coil 210 is an example of a first saddle coil employed according to the present invention. The connector 216 may be composed of two parallel electrical paths that do not cross but link the front loop 212 and rear loop 214 while running parallel to each other.

The saddle coil 210 is, as already known, electrically an inductance-capacitance (LC) circuit having capacitors connected in series with each other. The capacitors are not shown. Feeding power to the saddle coil 210 and receiving an electrical signal from the saddle coil 210 are, as already known, achieved across the capacitors, of which illustration will be omitted.

Figure 6:
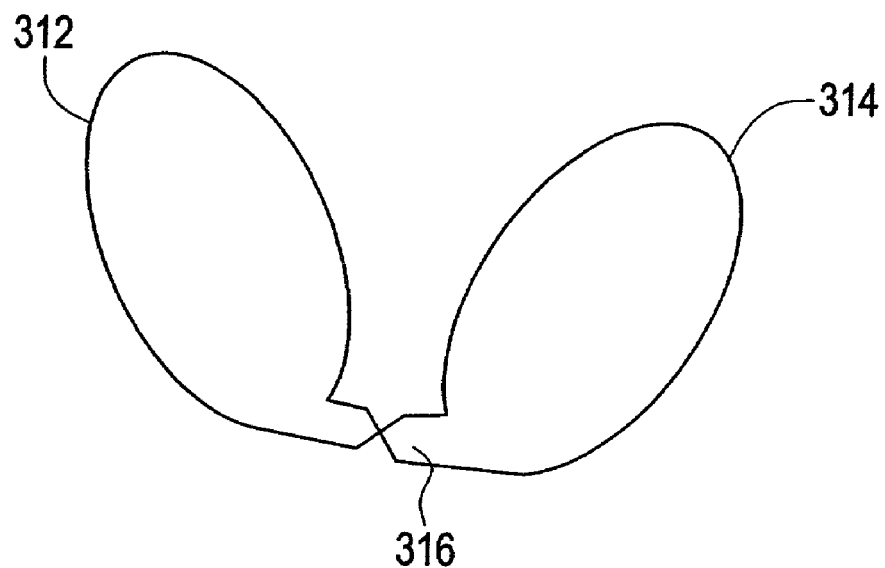
FIG. 6 schematically shows another saddle coil.

The RF coil assembly 110 includes a right loop 312 and a left loop 314 that permit insertion of the inferior limbs of a human body thereinto and that are opposed to each other with the inferior abdomen thereof sandwiched laterally between them. The right loop 312 and left loop 314 are linked by a connector 316. The connector 316 is, as shown in FIG. 6, composed of two crossing electrical paths, whereby, the right loop 312 and left loop 314 constitute a saddle coil 310 that is a closed loop. The saddle coil 310 is an example of a second saddle coil employed according to the present invention. The connector 316 may be composed of two parallel electrical paths that do not cross but link the right loop 312 and left loop 314 while running parallel to each other.

Incidentally, the saddle coil 310 is, as already known, electrically an LC circuit having capacitors connected in series with each other. The capacitors are not shown. Feeding power to the saddle coil 310 and receiving an electrical signal from the saddle coil 310 are, as already known, achieved across the capacitors, of which illustration will be omitted.

Figure 7:
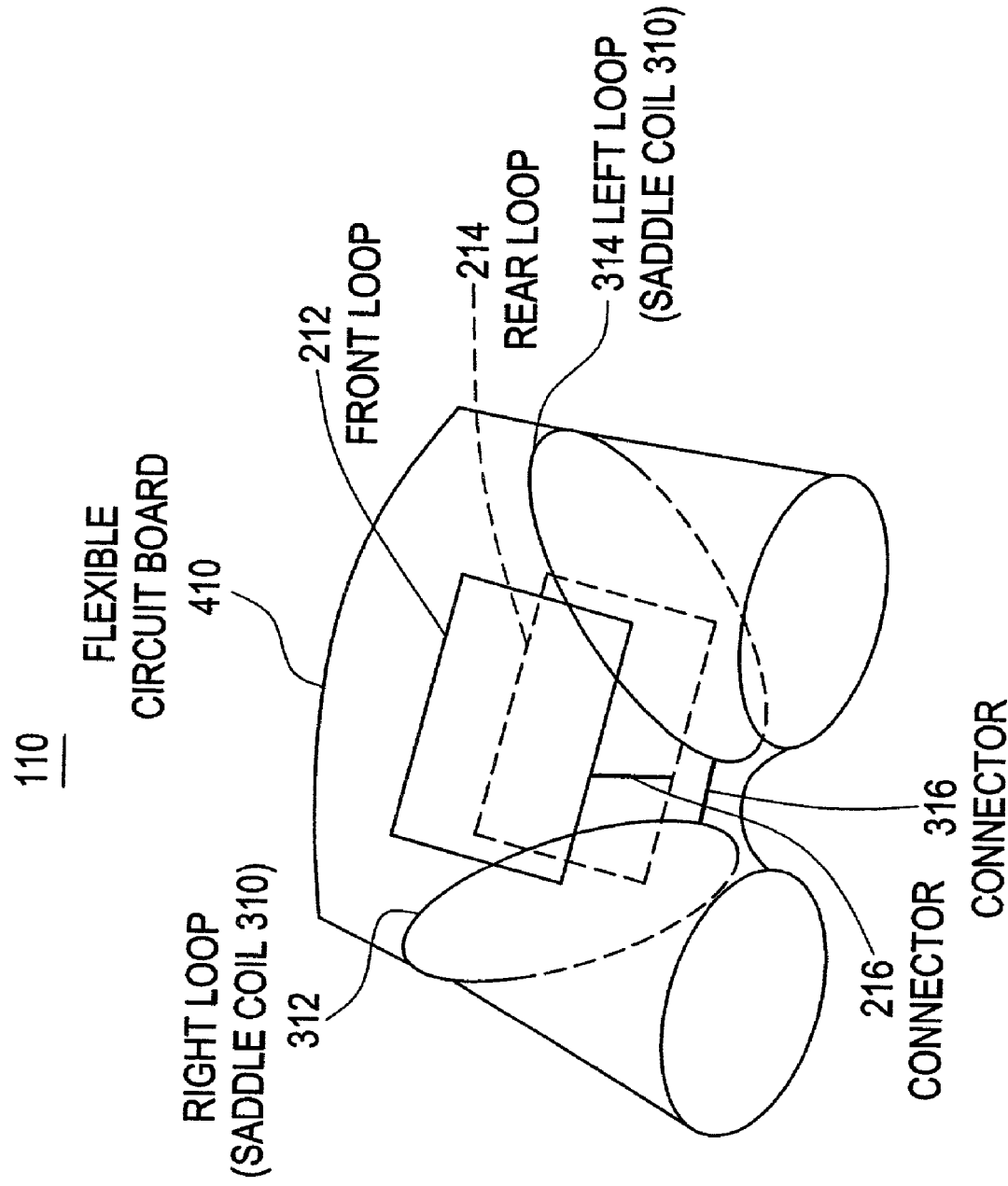
FIG. 7 schematically shows an RF coil.

The circuit patterns relevant to the saddle coil 210 and saddle coil 310 are, for example, printed on a flexible circuit board 410 as shown in FIG. 7. The flexible circuit board 410 is, as shown in FIG. 7, shaped like shorts so that it can be worn on the inferior abdomen of the object 1. The flexible circuit board 410 is an example of a flexible circuit board employed according to the present invention.

Figure 8:
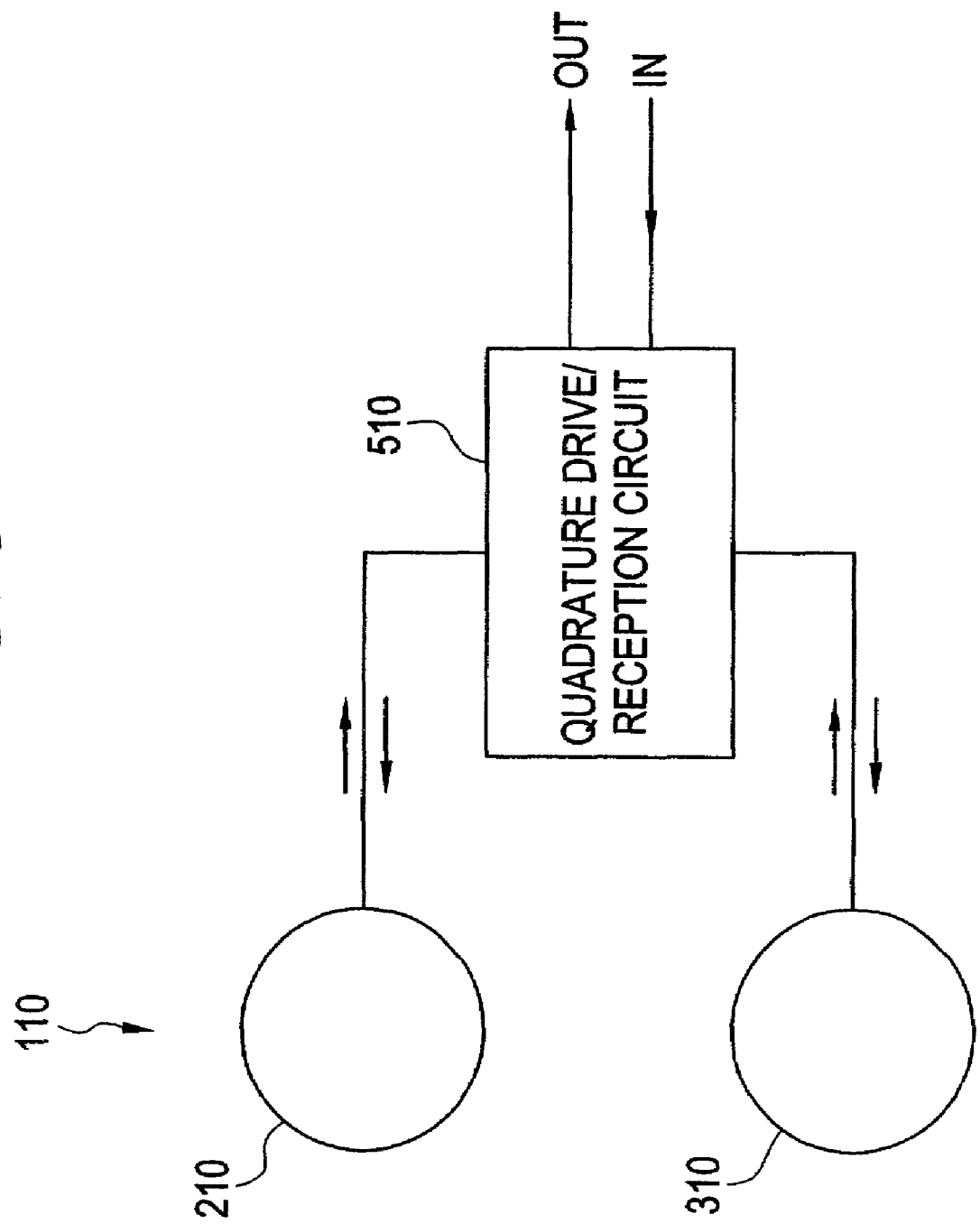
FIG. 8 is a block diagram showing an RF transmission/reception system.

FIG. 8 is a block diagram showing an electrical configuration to be adopted when the RF coil assembly 110 is used in common to transmit and receive RF signals. As illustrated, a quadrature drive/reception circuit 510 is connected to the saddle coils 210 and 310.

The drive circuit portion of the quadrature drive/reception circuit 510 corresponds to the RF drive unit 140 shown in FIG. 1. The reception circuit portion of the quadrature drive/reception circuit 510 corresponds to part of the data acquisition unit 150 shown in FIG. 1.

In order to transmit RF signals, the saddle coils 210 and 310 are driven with pulses that are in quadrature with each other and transmitted from the quadrature drive/reception circuit 510. In other words, the saddle coils 210 and 310 are driven with RF pulses that have a phase difference of 90° between them. The quadrature drive/reception circuit 510 is an example of a driving means employed according to the present invention. Moreover, the quadrature drive/reception circuit 510 is an example of a synthesizing means employed according to the present invention.

Magnetic resonance (MR) signals detected by the saddle coils 210 and 310 are received in quadrature with each other by the quadrature drive/reception circuit 510. In other words, two MR signals having a phase difference of 90° between them are detected by the saddle coils 210 and 310 respectively. A signal representing the sum of vectors proportional to the two MR signals is received. Thus, driving and receiving are achieved using the quadrature technique. This results in an improved signal-to-noise ratio relative to MR signals. Consequently, a high-quality image of the prostate can be produced.

Incidentally, the RF coil assembly 108 and RF drive unit 140 may be responsible for transmission of RF signals, and the saddle coils 210 and 310 and the quadrature drive/reception circuit 510 may be responsible for reception alone.

Figure 9:
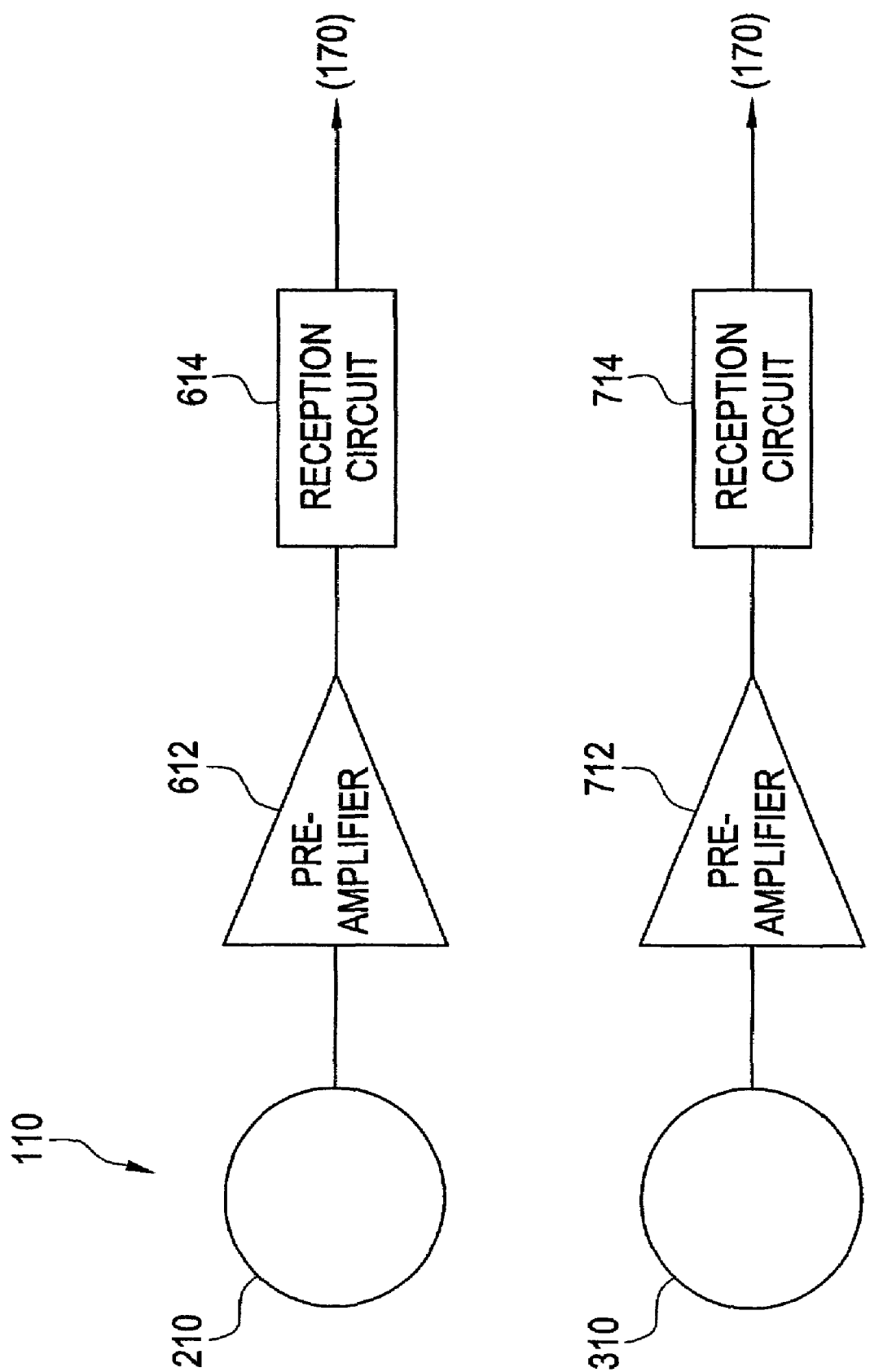
FIG. 9 is a block diagram showing an RF reception system.

FIG. 9 is a block diagram showing another example of an electrical configuration to be adopted when the RF coil assembly 110 is used exclusively for reception of RF signals. When the RF coil assembly 110 is used exclusively for reception, the RF coil assembly 108 and RF drive unit 140 transmit RF signals.

As illustrated, a signal received by the saddle coil 210 is amplified by a preamplifier 612 and transferred to a reception circuit 614. A signal received by the saddle coil 310 is amplified by a preamplifier 712 and transferred to a reception circuit 714. The signals received by the reception circuits 614 and 714 are transferred to the data processing unit 170. The data processing unit 170 synthesizes the signals according to a phased array technique. The data processing unit 170 is an example of a synthesizing means employed according to the present invention. The preamplifiers 612 and 712 and the reception circuits 614 and 714 correspond to part of the data acquisition unit 150.

As mentioned above, the signals received by the two saddle coils are synthesized according to the phased array technique. This results in an improved signal-to-noise ratio relative to magnetic resonance signals. Eventually, a high-quality image of the prostate can be produced.

Figure 10:
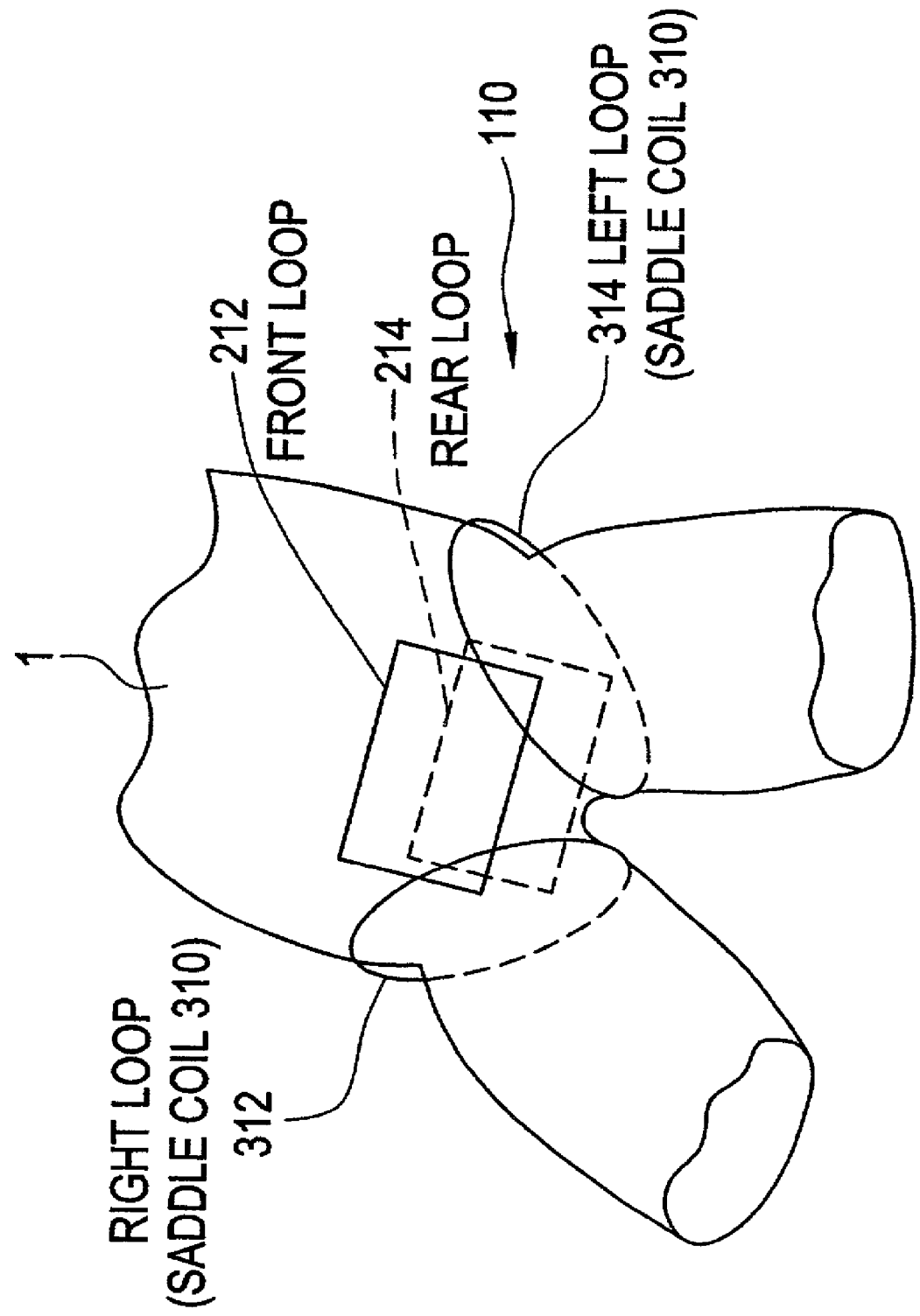
FIG. 10 schematically shows an RF coil worn on an object.

The front loop 212, rear loop 214, right loop 312, and left loop 314 may be, for example, as shown in FIG. 10, independent of one another. The front loop 212 and rear loop 214 constitute an example of a first coil pair employed according to the present invention. The right loop 312, and left loop 314 constitute an example of a second coil pair employed according to the present invention. These loops are preferably mounted on the flexible circuit board 410, which is shaped like shorts as shown in FIG. 7, in terms of ease of having the loops worn on the object 1.

Figure 11:
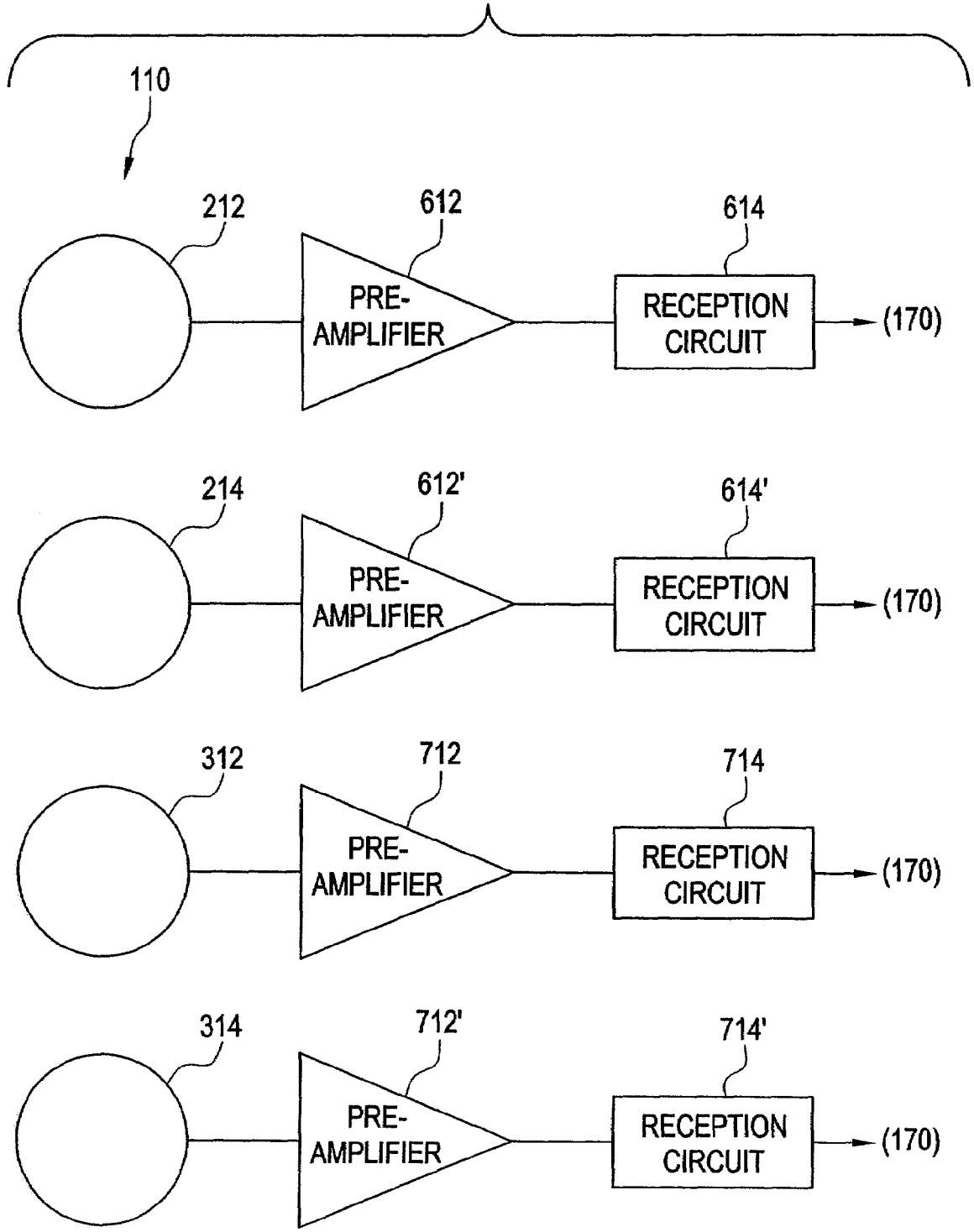
FIG. 11 is a block diagram showing an RF reception system.

Assuming that the loops are formed mutually independently, for example, as shown in FIG. 11, a reception system including a preamplifier and a reception circuit receives a signal detected by each loop. The data processing unit 170 synthesizes received signals according to the phased array technique.

A preferred embodiment of the present invention has been described by taking examples. People with an ordinary skill in the art to which the present invention belongs will be able to modify the examples or replace them with others without departing from the technological scope of the present invention. The technological scope of the present invention encompasses not only the examples of the preferred embodiment but also all embodiments that may be constructed based on claims.

Many widely different embodiments of the invention may be configured without departing from the spirit and the scope of the present invention. It should be understood that the present invention is not limited to the specific embodiments described in the specification, except as defined in the appended claims.

The invention claimed is:

1. An RF coil comprising:
   a first saddle coil having two loop portions opposed to each other, wherein said two loop portions of said first saddle coil configured to sandwich the inferior abdomen of a human body antero-posteriorly; and
   a second saddle coil having two loop portions opposed to each other, wherein said two loop portions of said second saddle coil configured to permit insertion of the inferior limbs of a human body thereinto and configured to sandwich the inferior abdomen thereof laterally, wherein one of said two loop portions of said second saddle coil comprises a single piece having a circumference configured to receive one of the inferior limbs.

2. An RF coil of claim 1, further comprising a flexible circuit board that is shaped to be readily worn on the inferior abdomen of a human body and that has a circuit pattern relevant to said first saddle coil and a circuit pattern relevant to said second saddle coil printed thereon.

3. An RF coil comprising:
a first coil pair having two loops opposed to each other, wherein said two loops of said first coil pair configured to sandwich the inferior abdomen of a human body antero-posteriorly; and
a second coil pair having two loops opposed to each other, wherein said two loops of said second coil pair configured to permit insertion of the inferior limbs of a human body thereinto and configured to sandwich the inferior abdomen thereof laterally, wherein one of said two loops of said second coil pair comprises a single piece having a circumference configured to receive one of the inferior limbs.

4. An RF coil of claim 3, further comprising a flexible circuit board that is shaped to be readily worn on the inferior abdomen of a human body and that has a circuit pattern relevant to said first coil pair and a circuit pattern relevant to said second coil pair printed thereon.

5. An RF signal transmitter-receiver comprising:
a first saddle coil having two loop portions opposed to each other, wherein said two loop portions of said first saddle coil configured to sandwich the inferior abdomen of a human body antero-posteriorly;
a second saddle coil having two loop portions opposed to each other, wherein said two loop portions of said second saddle coil configured to permit insertion of the inferior limbs of a human body thereinto and configured to sandwich the inferior abdomen thereof laterally;
a driving device for driving said first saddle coil and said second saddle coil using a quadrature technique; and
a synthesizing device for synthesizing two RF signals received by said first saddle coil and said second saddle coil respectively using the quadrature technique.

6. An RF signal transmitter-receiver of claim 5, further comprising a flexible circuit board that is shaped to be readily worn on the inferior abdomen of a human body and that has a circuit pattern relevant to said first saddle coil and a circuit pattern relevant to said second saddle coil printed thereon.

7. An RF signal receiver comprising:
a first saddle coil having two loop portions opposed to each other, wherein said two loop portions of said first saddle coil configured to sandwich the inferior abdomen of a human body antero-posteriorly;
a second saddle coil having two loop portions opposed to each other, wherein said two loop portions of said second saddle coil configured to permit insertion of the inferior limbs of a human body thereinto and configured to sandwich the inferior abdomen thereof laterally; and
a synthesizing device for synthesizing two RF signals received by said first saddle coil and said second saddle coil respectively using a quadrature technique.

8. An RF signal receiver comprising:
a first saddle coil having two loop portions opposed to each other, wherein said two loop portions of said first saddle coil configured to sandwich the inferior abdomen of a human body antero-posteriorly;
a second saddle coil having two loop portions opposed to each other, wherein said two loop portions of said second saddle coil configured to permit insertion of the inferior limbs of a human body thereinto and configured to sandwich the inferior abdomen thereof laterally; and
a synthesizing device for synthesizing two RF signals received by said first saddle coil and said second saddle coil respectively using a phased array technique.

9. An RF signal receiver of claim 7, further comprising a flexible circuit board that is shaped to be readily worn on the inferior abdomen of a human body and that has a circuit pattern relevant to said first saddle coil and a circuit pattern relevant to said second saddle coil printed thereon.

10. An RF signal receiver comprising:
a first coil pair having two loops opposed to each other, wherein said two loops of said first coil pair configured to sandwich the inferior abdomen of a human body antero-posteriorly;
a second coil pair having two loops opposed to each other, wherein said two loops of said second coil pair configured to permit insertion of the inferior limbs of a human body thereinto and configured to sandwich the inferior abdomen thereof laterally; and
a synthesizing device for synthesizing two RF signals received by said first coil pair and said second coil pair respectively using a phased array technique.

11. An RF signal receiver of claim 10, further comprising a flexible circuit board that is shaped to be worn on the inferior abdomen of a human body and that has a circuit pattern relevant to said first coil pair and a circuit pattern relevant to said second coil pair printed thereon.

12. A magnetic resonance imaging system comprising:
a static magnetic field creating device for creating a static magnetic field in a space in which an object of imaging is placed;
a magnetic field gradient creating device for creating magnetic field gradients in said space;
an RF signal transmitting/receiving device for transmitting RF signals to said space and receiving RF signals from said space; and
an image producing device for producing an image according to the received RF signals,
wherein said RF signal transmitting/receiving device comprises:
a first saddle coil having two loop portions opposed to each other, wherein said two loop portions of said first saddle coil configured to sandwich the inferior abdomen of a human body antero -posteriorly;
a second saddle coil having two loop portions opposed to each other, wherein said two loop portions of said second saddle coil configured to permit insertion of the inferior limbs of a human body thereinto and configured to sandwich the inferior abdomen thereof laterally;
a driving device for driving said first saddle coil and said second saddle coil using a quadrature technique; and
a synthesizing device for synthesizing two RF signals received by said first saddle coil and said second saddle coil respectively using the quadrature technique.

13. A magnetic resonance imaging system of claim 12, further comprising a flexible circuit board that is shaped to be readily worn on the inferior abdomen of a human body and that has a circuit pattern relevant to said first saddle coil and a circuit pattern relevant to said second saddle coil printed thereon.

14. A magnetic resonance imaging system comprising:
a static magnetic field creating device for creating a static magnetic field in a space in which an object of imaging is placed;
a magnetic field gradient creating device for creating magnetic field gradients in said space;
an RF signal transmitting device for transmitting RF signals to said space;
an RF signal receiving device for receiving RF signals from said space;
an image producing device for producing an image according to the received RF signals,
wherein said RF signal receiving device comprises:
a first saddle coil having two loop portions opposed to each other, wherein said two loop portions of said first saddle coil configured to sandwich the inferior abdomen of a human body antero-posteriorly;
a second saddle coil having two loop portions opposed to each other, wherein said two loop portions of said second saddle coil configured to permit insertion of the inferior limbs of a human body thereinto and configured to sandwich the inferior abdomen thereof laterally; and
a synthesizing device for synthesizing two RF signals received by said first saddle coil and said second saddle coil respectively using a quadrature technique.

15. A magnetic resonance imaging system comprising:
a static magnetic field creating device for creating a static magnetic field in a space in which an object of imaging is placed;
a magnetic field gradient creating device for creating magnetic field gradients in said space;
an RF signal transmitting device for transmitting RF signals to said space;
an RF signal receiving device for receiving RF signals from said space; and
an image producing device for producing an image according to the received RF signals,
wherein said RF signal receiving device comprises:
a first saddle coil having two loop portions opposed to each other, wherein said two loop portions of said first saddle coil configured to sandwich the inferior abdomen of a human body antero -posteriorly;
a second saddle coil having two loop portions opposed to each other, wherein said two loop portions of said second saddle coil configured to permit insertion of the inferior limbs of a human body thereinto and configured to sandwich the inferior abdomen thereof laterally; and
a synthesizing device for synthesizing two RF signals received by said first saddle coil and said second saddle coil respectively using a phased array technique.

16. A magnetic resonance imaging system of claim 14, further comprising a flexible circuit board that is shaped to be readily worn on the inferior abdomen of a human body and that has a circuit pattern relevant to said first saddle coil and a circuit pattern relevant to said second saddle coil printed thereon.

17. A magnetic resonance imaging system comprising:
a static magnetic field creating device for creating a static magnetic field in a space in which an object of imaging is placed;
a magnetic field gradient creating device for creating magnetic field gradients in said space;
an RF signal transmitting device for transmitting RF signals to said space;
an RF signal receiving device for receiving RF signals from said space; and
an image producing device for producing an image according to the received RF signals,
wherein said RF signal receiving device comprises:
a first coil pair having two loops opposed to each other wherein said two loops of said first coil pair configured to sandwich the inferior abdomen of a human body antero-posteriorly;
a second coil pair having two loops opposed to each other, wherein said two loop portions of said second saddle coil configured to permit insertion of the inferior limbs of a human body thereinto and configured to sandwich the inferior abdomen thereof laterally; and
a synthesizing device for synthesizing two RF signals received by said first coil pair and said second coil pair respectively using a phased array technique.

18. A magnetic resonance imaging system of claim 17, further comprising a flexible circuit board that is shaped to be worn on the inferior abdomen of a human body and that has a circuit pattern relevant to said first coil pair and a circuit pattern relevant to said second coil pair printed thereon.

19. An RF signal receiver of claim 8, further comprising a flexible circuit board that is shaped to be readily worn on the inferior abdomen of a human body and that has a circuit pattern relevant to said first saddle coil and a circuit pattern relevant to said second saddle coil printed thereon.

20. A magnetic resonance imaging system of claim 15, further comprising a flexible circuit board that is shaped to be readily worn on the inferior abdomen of a human body and that has a circuit pattern relevant to said first saddle coil and a circuit pattern relevant to said second saddle coil printed thereon.

* * * * *